United States Patent
Conway

[11] Patent Number: 5,819,317
[45] Date of Patent: Oct. 13, 1998

[54] INFANT T-SHIRT

[75] Inventor: David W. Conway, Loveland, Ohio

[73] Assignee: Intellitecs International Ltd., Cincinnati, Ohio

[21] Appl. No.: 575,623

[22] Filed: Dec. 20, 1995

[51] Int. Cl.⁶ .......................... A41B 13/04; A41D 11/00
[52] U.S. Cl. .................... 2/111; 2/75; 2/80; 2/83; 2/69
[58] Field of Search .......................... 2/75, 80, 83, 107, 2/117, 111, 112, 78.2, 400, 401, 403, 406, 408, 78.1, 78.3, 78.4, 69, 69.5, 243.1; 450/102; 11/103; 604/385.1

[56] References Cited

U.S. PATENT DOCUMENTS

| | | |
|---|---|---|
| Re. 30,972 | 6/1982 | Kyle et al. . |
| 645,488 | 3/1900 | Osgood ......................................... 2/111 |
| 881,640 | 3/1908 | Wimmel ....................................... 2/111 |
| 1,083,712 | 1/1914 | Uyeda .......................................... 2/408 |
| 1,260,873 | 3/1918 | Colman ..................................... 2/111 X |
| 1,672,661 | 6/1928 | Tilden .......................................... 2/111 |
| 2,016,664 | 10/1935 | Brewster ...................................... 2/112 |
| 2,664,895 | 1/1954 | Shulman . |
| 2,671,220 | 3/1954 | Gerssmann ................................... 2/111 |
| 3,208,451 | 9/1965 | Porter et al. . |
| 3,375,827 | 4/1968 | Beltzinger et al. . |
| 3,563,243 | 2/1971 | Lindquist . |
| 3,720,212 | 3/1973 | Kaupin . |
| 3,721,242 | 3/1973 | Krusko . |
| 3,863,637 | 2/1975 | MacDonald et al. . |
| 3,882,871 | 5/1975 | Taniguchi et al. . |
| 3,888,256 | 6/1975 | Studinger . |
| 4,021,870 | 5/1977 | Walters . |
| 4,352,356 | 10/1982 | Tong . |
| 4,637,078 | 1/1987 | Southwell .................................... 2/408 |
| 4,850,987 | 7/1989 | Gilomen . |
| 4,981,480 | 1/1991 | Gaudet et al. . |
| 5,065,600 | 11/1991 | Byles . |
| 5,210,882 | 5/1993 | Moretz et al. . |
| 5,217,782 | 6/1993 | Moretz et al. . |
| 5,241,710 | 9/1993 | Lockhart .................................. 2/408 X |
| 5,249,320 | 10/1993 | Moretz et al. . |
| 5,261,901 | 11/1993 | Guay . |
| 5,290,269 | 3/1994 | Heiman . |
| 5,291,617 | 3/1994 | Moretz et al. . |
| 5,296,290 | 3/1994 | Brassington . |
| 5,297,296 | 3/1994 | Moretz et al. . |
| 5,306,536 | 4/1994 | Moretz et al. . |
| 5,315,717 | 5/1994 | Moretz et al. . |
| 5,367,709 | 11/1994 | Teasley ......................................... 2/83 |
| 5,392,467 | 2/1995 | Moretz et al. . |
| 5,414,870 | 5/1995 | Moretz et al. . |
| 5,435,014 | 7/1995 | Moretz et al. . |

FOREIGN PATENT DOCUMENTS

WO 8605386  9/1986  WIPO .

*Primary Examiner*—Jeanette E. Chapman
*Attorney, Agent, or Firm*—Wood, Herron & Evans L.L.P.

[57] ABSTRACT

An infant T-shirt (10) is provided with an improved crotch panel (14) having an absorbent layer (50) and a barrier layer (52) to retain fluids. The absorbent layer (50) may have an upper hydrophobic surface (54) and a lower hydrophilic surface (56). The barrier layer (52) may have a fluid barrier ply (60) and a fabric ply (62) to support the fluid barrier ply (60). The fabric ply (62) may define the outer surface of the crotch panel (14). Alternatively, an extension (80) of the T-shirt material may define that outer surface with the barrier layer (52) overlying the extension (80).

5 Claims, 1 Drawing Sheet

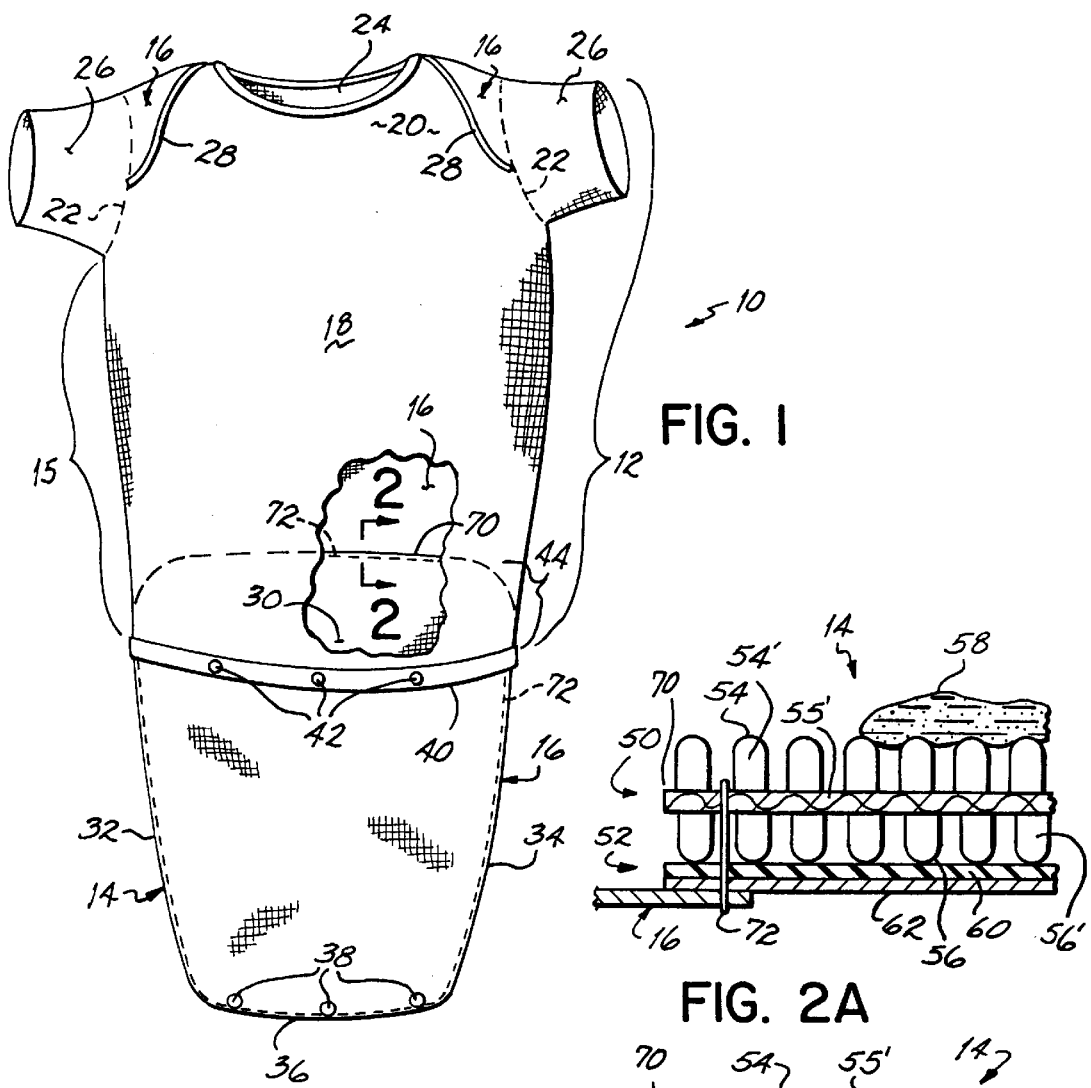
FIG. 1
FIG. 2A
FIG. 2B
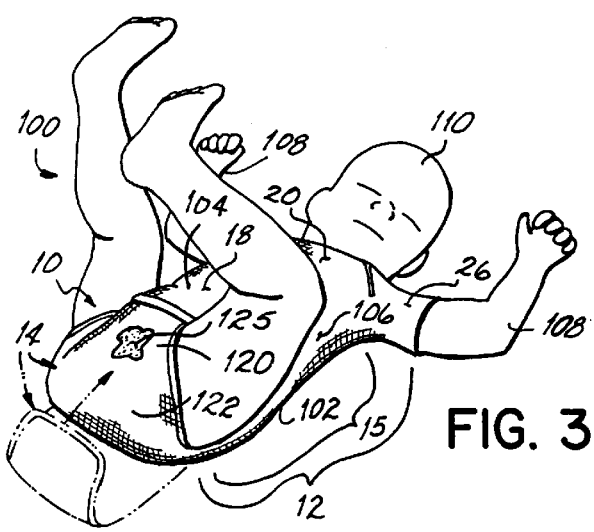
FIG. 3

INFANT T-SHIRT

BACKGROUND OF THE INVENTION

I. Field of the Invention

The present invention relates to infant T-shirts and, more specifically, to such T-shirts which have a crotch panel.

II. Description of the Prior Art

Infant T-shirts are well known and have a shirt section in which the front and back sides of the shirt are interconnected to define a body casing that fits about the infant's torso. The body casing is provided at its upper end with arm holes and a neck opening. Many of these T-shirts further include a crotch panel which extends from the back side of the T-shirt through the infant's legs and up over to the front side of the T-shirt. Usually, the crotch panel is fastened to the front side of the T-shirt by snaps or other releasable catches so that a diaper, for example, may be changed without removing the entire T-shirt.

T-shirts having crotch panels are often used with infants who are also wearing diapers. As a consequence, when the diaper fails for any reason, urine or other liquids from the infant will leak over the diaper edges, especially in the area of the crotch, and seep into the T-shirt crotch panel, thereby soiling same. Worse yet, the fluids will tend to leak directly past the T-shirt crotch panel. In some cases, the fluids will leak into the upper shirt portions of the T-shirt making the infant uncomfortable. Also, fluids may leak into the outer clothing being worn by the infant or onto other persons holding or playing with the infant.

SUMMARY OF THE INVENTION

The present invention provides an infant T-shirt with a crotch panel designed to retain overrun of urine or other fluids such as from a diaper so as to minimize discomfort to the infant, soiling of outer clothing, and/or leakage onto another person. To this end, and in accordance with the principles of the present invention, the crotch panel includes a fluid absorbent fabric designed to retain the excess fluid, as well as a fluid barrier layer to prevent excess fluids from passing through the crotch panel and into the outer clothing or onto another person. Also, the excess fluids are held in the crotch panel and so will not soil others when the T-shirt is removed. The materials making up the crotch panel are washable so the T-shirt may be washed and reused as in the case of conventional infant T-shirts, but without the drawbacks noted above.

In a preferred embodiment, the absorbent layer is comprised of a single, integral piece of dual purpose fabric in which an upper surface facing the infant has hydrophobic qualities and a lower surface facing away from the infant has hydrophilic properties. With such a fabric, the excess fluid is wicked from the inner surface of the crotch panel and towards the lower or hydrophilic surface of the absorbent layer wherein the excess fluid will be retained to thus minimize discomfort to the infant. In this regard, the surface of the crotch panel adjacent the infant has a "dry feel" to it. Moreover, fluid is retained in the absorbent fabric rather than leaking into the rest of the T-shirt. The fluid is also prevented from leaking into the crotch panel outer surface by the barrier layer to thus avoid leaking onto outer clothing or another person. Further preferably, the barrier layer is comprised of a fluid barrier web attached to and supported on an outer fabric web. The outer fabric web supporting the fluid barrier web may define the outer surface of the crotch panel. Alternatively, the outer surface of the crotch panel may be a continuation of the T-shirt material with the barrier layer outer fabric web secured directly thereagainst in confronting relationship.

By virtue of the foregoing, there is thus provided an infant T-shirt having a fluid-retaining crotch panel so as to retain excess fluids from a diaper or the like without causing discomfort to the infant or soiling outer clothing or another person. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

FIG. 1 is a front, partially broken away view of an infant T-shirt having a crotch panel incorporating the features of the present invention;

FIG. 2A is an enlarged schematic view taken along line 2—2 of FIG. 1 showing a first embodiment of the crotch panel;

FIG. 2B is also a view taken along line 2—2 of FIG. 1 showing a second alternative embodiment of the crotch panel; and FIG. 3 is a perspective, partially broken away view of an infant wearing the T-shirt of FIG. 1.

DETAILED DESCRIPTION OF THE DRAWINGS

With reference to FIG. 1, there is shown an infant T-shirt 10 having a shirt section 12 and a crotch panel 14 incorporating the features of the present invention. To this end, shirt section 12 is of generally typical construction having a tubular body casing 15 which is defined by interconnected back web 16 and front web 18 which in use would overlie the back 102 and chest/belly 104 areas, respectively, of the infant's upper torso 106 (see FIG. 3). Situated near the upper end 20 of webs 16 and 18 are arm holes 22 and neck hole 24 to receive the arms 108 and head 110, respectively, of the infant 100 therethrough. Sleeves 26 may be attached to body casing 15 at arm holes 22 as is also conventional. Further, back web 16 may be connected to front web 18 at upper end 20 in overlapping arrangement as at 28 in FIG. 1.

Crotch panel 14 of T-shirt 10 extends from adjacent lower end 30 of shirt section back web 16 and is tapered slightly along its edges 32,34 to fit within an infant's crotch 120. Panel 14 terminates along edge 36 and is provided with a plurality of female snap receivers 38 therealong. Situated along lower end 40 of shirt section front web 18 is a plurality of mating male snaps 42 such that crotch panel 14 may be selectively connected to web 18 and snapped closed around the crotch area 120 of an infant 100 or opened to allow removal of a diaper 125, for example, without requiring removal of T-shirt 10. Crotch panel 14 may advantageously include the lower segment 44 of back web 16 which would underlie the infant's buttocks 122.

To provide the advantages of the present invention, and with reference to FIG. 2A, crotch panel 14 has an upper or inner fluid absorbing layer 50 and a lower or outer fluid barrier layer 52. Absorbent layer 50 is positioned uppermost in crotch panel 14 so as to face the infant's crotch area 120, with barrier layer 52 positioned therebelow.

Absorbent layer 50 may preferably be provided by a single piece of dual purpose fabric in which the uppermost surface 54 facing the infant 100 has hydrophobic properties, and the lowermost surface 56 has hydrophilic properties such that any excess fluid 58 impinging upon upper surface 54 would be wicked away and towards hydrophilic surface 56 of layer 50 to be retained therein and away from the infant's body. Further, hydrophilic layer 56 retains fluid to minimize the likelihood that any of the fluids would wick up into either front web 18 or back web 16 of T-shirt 10. Absorbent layer 50 may be an integral single layer having polyester or polypropylene pile yarns 54' defining upper hydrophobic surface 54 and cotton pile yarns 56' defining lower hydrophilic surface 56 connected with a ground yarn 55' in the manner shown and described in FIGS. 3 and 8, and the accompanying text, of U.S. Pat. No. 5,290,296.

Barrier layer 52 is provided to prevent excess fluid retained in absorbent layer 50 from passing through crotch panel 14 and out onto further clothing layers or another person (both not shown). Barrier layer 52 may preferably be provided by a first fluid barrier ply 60 such as a polyurethane web and a second ply 62 such as a polyester tricot knit fabric web. Barrier ply 60 is preferably glued or otherwise laminated to fabric ply 62 or may be coated or extruded thereon. The above-described preferred absorbent layer 50 and barrier layer 52 have their lower surface 56 and upper ply 60 secured into confronting relationship and may be provided by a section of incontinent pad such as described in FIGS. 1–4 and 8, and the accompanying description thereof, of U.S. Pat. No. 5,290,269. The entire disclosure of U.S. Pat. No. 5,290,269 is incorporated herein by reference.

In the embodiment shown in FIG. 2A, the outer tricot ply 62 also defines the outer surface of crotch panel 14. To this end, back edge 70 of crotch panel 14 (defined by combined layers 50 and 52) is stitched (such as with polyester or polypropylene threads 72) or otherwise joined to shirt section back web 16 along the lower end 30 thereof (at or above the infant's buttocks 122). Stitching with the same type of threads is also provided along edges 32,34 and front end 36 to secure layers 50 and 52 together, and female snap receivers 38 are provided along front edge 36.

In an alternative embodiment shown in FIG. 2B, crotch panel 14 includes a further, outer layer or ply 80 defined by an integral, elongated extension of shirt section back web 16 as would be provided in a conventional T-shirt with crotch panel. The absorbent and barrier layers 50 and 52 are secured to the shirt ply 80 with the barrier layer fabric ply 62 confronting extension 80 (and thus being sandwiched between extension 80 and absorbent layer 50) such as by stitching with threads 72 along the back side and front edges (70, 32, 34 and 30) of layers 50 and 52 and the adjacent areas of crotch panel ply 80. In the alternative embodiment of FIG. 2B, the edges of absorbent and barrier layers 50,52 may be inboard of the edges of web extension 80 if desired. Further, back edge 56 of crotch panel 14 is integrally formed with back web 16 so as to be connected thereto in an integral fashion rather than being separately sewn or otherwise held thereto as in the case of the embodiment shown in FIG. 2A.

The materials of crotch panel 14 in either embodiment are preferably washable so that T-shirt 10 provided with the improved crotch panel as above-described may be washed and reused several times.

In use, and as seen in FIG. 3, the infant 100 is fitted with T-shirt 10 in conventional manner and crotch panel 14 is passed from under the infant's buttocks 122 up through the crotch area 120 and fastened by the snaps 38,42. Preferably, crotch panel 14 is closed after a diaper 125 has been placed upon the infant. Thereafter, outer clothing may optionally be provided. Excess fluid from the diaper, should there be leakage, will pass into absorbent layer 50 and be wicked from upper surface 54 thereof towards the lower surface 56 and limited by action of barrier layer 52 until T-shirt 10 is removed and washed, for example. The fluid retention properties of the improved crotch panel 14 will tend to retain the excess fluid to thus prevent it from wicking out into the back or front webs 16, 18 making the infant uncomfortable and also preventing seepage or strike-through for fluid to soil outer clothing or other persons. As will be readily apparent, crotch panel 14 may be selectively opened to facilitate removal of diaper 125 or removal of T-shirt 10.

By virtue of the foregoing, there is thus provided an infant T-shirt with an improved crotch panel to reduce the likelihood of discomfort to an infant and/or soiling of outer clothing or other persons in the event that excess fluid is not retained by a diaper or the like being worn by the infant.

While the present invention has been illustrated by description of embodiments, and while the illustrative embodiments have been described in considerable detail, it is not the intention of applicant to restrict or in any way limit the scope of the appended claims to such detail. Additional advantages and modifications will readily appear to those skilled in the art. For example, lower surface 56 of absorbent layer 50 is not normally adhered to barrier layer 52 except along the peripheral edges thereof where they are typically sewn together. However, and alternatively, layers 50 and 52 may be laminated together if desired. Further, snap members 38, 42 may be replaced with other means for selectively connecting the front edge 38 of the crotch panel 14 to the lower end of shirt section front web 18. By way of example, Velcro® fasteners, tapes, safety pins, or hooks may be used. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method of dressing an infant, comprising:

positioning a diaper over a crotch area of said infant, providing an infant T-shirt comprising a shirt section having interconnected back and front webs to define a body casing including arm holes and a neck hole, and a crotch panel having a fluid absorbent layer overlying a fluid barrier layer, positioning the torso of said infant within said body casing with the arms and neck of the infant extending into said arm and neck holes, positioning said fluid absorbent layer of said crotch panel of said infant T-shirt in confronting relationship to the diaper in the crotch area of said infant, and connecting said crotch panel of said infant T-shirt to at least one of said webs of said shirt section such that said crotch panel overlies said diaper.

2. The method of claim 1 wherein providing said crotch panel of said infant T-shirt comprises providing an absorbent layer having upper and lower surfaces, the upper surface having hydrophobic properties and the lower surface having hydrophilic properties, whereby fluids at the upper surface tend to wick towards the lower surface of the absorbent layer, and positioning said fluid absorbent layer in confronting relationship to the diaper in the crotch area of said infant comprises positioning the hydrophobic surface in confronting relationship to the diaper.

3. The method of claim 2 wherein providing said fluid barrier layer comprises providing a fluid barrier layer having first and second plies, the first ply being a web of fluid barrier material and the second ply being a web of fabric.

4. The method of claim 1 wherein providing said fluid barrier layer comprises providing a fluid barrier layer having first and second plies, the first ply being a web of fluid barrier material and the second ply being a web of fabric.

5. The method of claim 1, wherein providing said infant T-shirt comprises providing an infant T-shirt having said crotch panel attached along a back edge to a lower end of the shirt section back web, and connecting said crotch panel of said infant T-shirt comprises detachably connecting a front edge of the crotch panel to a lower end of the shirt section front web.

* * * * *